United States Patent [19]

Corbett et al.

[11] 4,339,547

[45] Jul. 13, 1982

[54] PRODUCTION OF SYNTHETIC HYDROCARBONS FROM AIR, WATER AND LOW COST ELECTRICAL POWER

[75] Inventors: Marshall J. Corbett, East Northport; Salvatore C. Salina, Bethpage, both of N.Y.

[73] Assignee: Grumman Aerospace Corporation, Bethpage, N.Y.

[21] Appl. No.: 167,075

[22] Filed: Jul. 9, 1980

Related U.S. Application Data

[62] Division of Ser. No. 77,880, Sep. 21, 1979, Pat. No. 4,282,187.

[51] Int. Cl.³ .......................... C07C 29/15; C07C 1/20
[52] U.S. Cl. .................................. 518/728; 423/232; 423/437; 204/98; 204/128; 204/129; 585/733
[58] Field of Search .............. 423/437, 232; 518/728, 518/704; 585/733; 204/98, 129, 128

[56] References Cited

U.S. PATENT DOCUMENTS

| | | | |
|---|---|---|---|
| 3,037,844 | 6/1962 | Giammarco | 423/437 |
| 4,070,131 | 1/1978 | Yen | 415/3 |
| 4,075,500 | 2/1978 | Oman | 290/55 |

OTHER PUBLICATIONS

Payne et al., Industrial & Eng. Chem., vol. 24, (1932), pp. 630–637.

Primary Examiner—Bernard Helfin
Attorney, Agent, or Firm—Pollock, Vande Sande & Priddy

[57] ABSTRACT

A process for manufacturing synthetic hydrocarbons such as gasoline and/or kerosene from the synthesis of carbon dioxide and hydrogen. The carbon dioxide is obtained from the atmosphere while the hydrogen is obtained during the electrolysis of water. An intermediate fuel, namely methyl alcohol may be stored for use or upgraded to higher heating value hydrocarbons by a catalytic conversion.

7 Claims, 4 Drawing Figures

| SYN. GAS COMPONENT | PROCESS & EQUATION | EQUIPMENT |
|---|---|---|
| (a) HYDROGEN | ELECTROLYSIS OF WATER $2H_2O \xrightarrow{e} 2H_2 + O_2$ | ELECTROLYTIC CELLS |
| (b) CARBON DIOXIDE<br>— SODIUM HYPOCARBONATE & SODIUM BICARBONATE | $CO_2$ ABSORPTION<br>$2NaOH + CO_2 \rightarrow Na_2CO_3 + H_2O$<br>$CO_2 + Na_2CO_3 + H_2O \rightarrow 2NaHCO_3$ | SPRAY ABSORPTION TOWERS |
| (c) — CARBON DIOXIDE | $CO_2$ STRIPPING<br>$Na_2CO_3 + Cl_2 \rightarrow NaCl + NaOCl + CO_2$<br>$2NaHCO_3 + Cl_2 \rightarrow NaCl + NaOCl + 2CO_2 + H_2O$ | STRIPPING TOWER |
| (d) — SODIUM CHLORIDE | OXYGEN SEPARATOR<br>$2NaOCl \xrightarrow{\Delta} 2NaCl + O_2$ | BOILER |
| (e) — CAUSTIC/CHLORINE | CHLOR-ALKALI ELECTROLYSIS<br>$2H_2O + 2NaCl \xrightarrow{e} 2NaOH + Cl_2 + H_2$ | ELECTROLYTIC CELLS |
| (f) METHANOL | $CO_2 + 3H_2 \rightarrow CH_3OH + H_2O$ | METHANOL SYN. |
| (g) GASOLINE | $n CH_3OH \rightarrow (CH_2)_n + n H_2O$ | HYDROCARBON SYN. |

FIG. 2

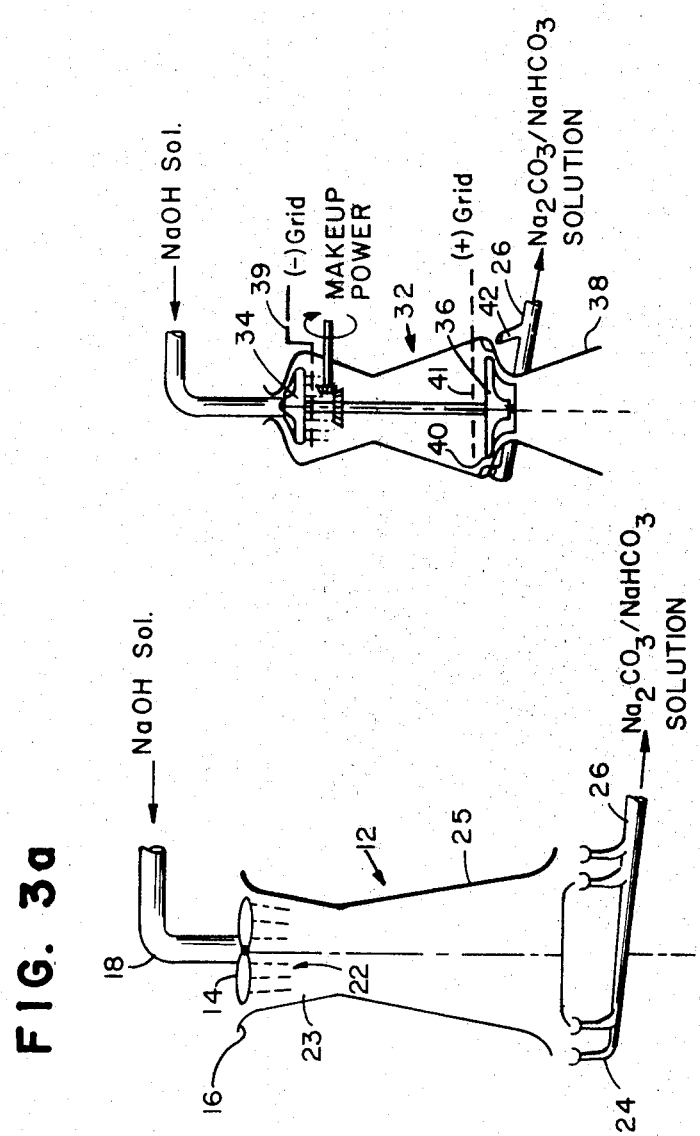

PRODUCTION OF SYNTHETIC HYDROCARBONS FROM AIR, WATER AND LOW COST ELECTRICAL POWER

This is a division, of application Ser. No. 77,880, filed Sept. 21, 1979 and now U.S. Pat. No. 4,282,187.

BACKGROUND OF THE INVENTION

1. Field of the Invention

The present invention relates to the production of synthetic hydrocarbons and more particularly to a process for hydrocarbon synthesis from $CO_2$ and $H_2$, derived from environmental matter, which produces methanol which may be upgraded to gasoline grade fuel.

2. Brief Description of the Prior Art

The production of methyl alcohol ($CH_3OH$) from compressed hydrogen ($H_2$) and carbon dioxide ($CO_2$) is known technology. In the process for producing methyl alcohol, the $H_2$ and $CO_2$ are admitted to a converter containing a copper catalyst which accelerates the combination of the two gases to produce the methyl alcohol (methanol). This process is disclosed in the Aug. 20, 1973, edition of Chemical Engineering Magazine (page 112). Test results from this process have been reported as producing a product which, after refining, is said to be 99.96 percent pure methanol. It is also known in the prior art to introduce pure methanol into a hydrocarbon synthesis reactor where a zeolite catalyst removes its water constituent, and synthesizes multiple hydrocarbon fuels having an average molecular weight which is dependent upon the pore size of the catalyst. The process for methanol conversion to hydrocarbons is the subject matter of an article appearing in the February, 1976, edition of Chemtech Magazine.

To date, the production of methanol and subsequent conversion to hydrocarbon fuels has employed rather time-consuming and costly chemical processes. Significant commercial significance can only be realized if low cost and plentiful supplies of $H_2$ and $CO_2$ are supplied.

BRIEF DESCRIPTION OF THE PRESENT INVENTION

The process of the present invention produces synthetic hydrocarbons, such as gasoline and/or kerosene from the synthesis of $CO_2$ obtained from environmental matter such as air in the atmosphere, and from $H_2$ also obtained from environmental matter, such as from the electrolysis of water. An intermediate fuel, namely methanol, is first produced and then upgraded to higher heating value hydrocarbons by a terminal catalytic step. The $CO_2$ is available in an almost unlimited quantity from the atmosphere or natural water bodies, such as rivers, lakes and oceans which may also provide a source of $H_2$ after electrolysis. Thus, the basic chemical components necessary for the present process are readily available, in virtually unlimited quantity and at relatively low cost.

The above-mentioned objects and advantages of the present invention will be more clearly understood when considered in conjunction with the accompanying drawings, in which:

BRIEF DESCRIPTION OF THE FIGURES

FIG. 2 is a table detailing the chemical reactions which occur at each step of the present inventive process.

FIG. 3a is a mechanical schematic view of the basic internal structure of a first embodiment of a $CO_2$ absorption tower.

FIG. 3b is a mechanical schematic view of the basic internal structure of a second embodiment of a $CO_2$ absorption tower.

DETAILED DESCRIPTION OF THE INVENTION

Figure 1:
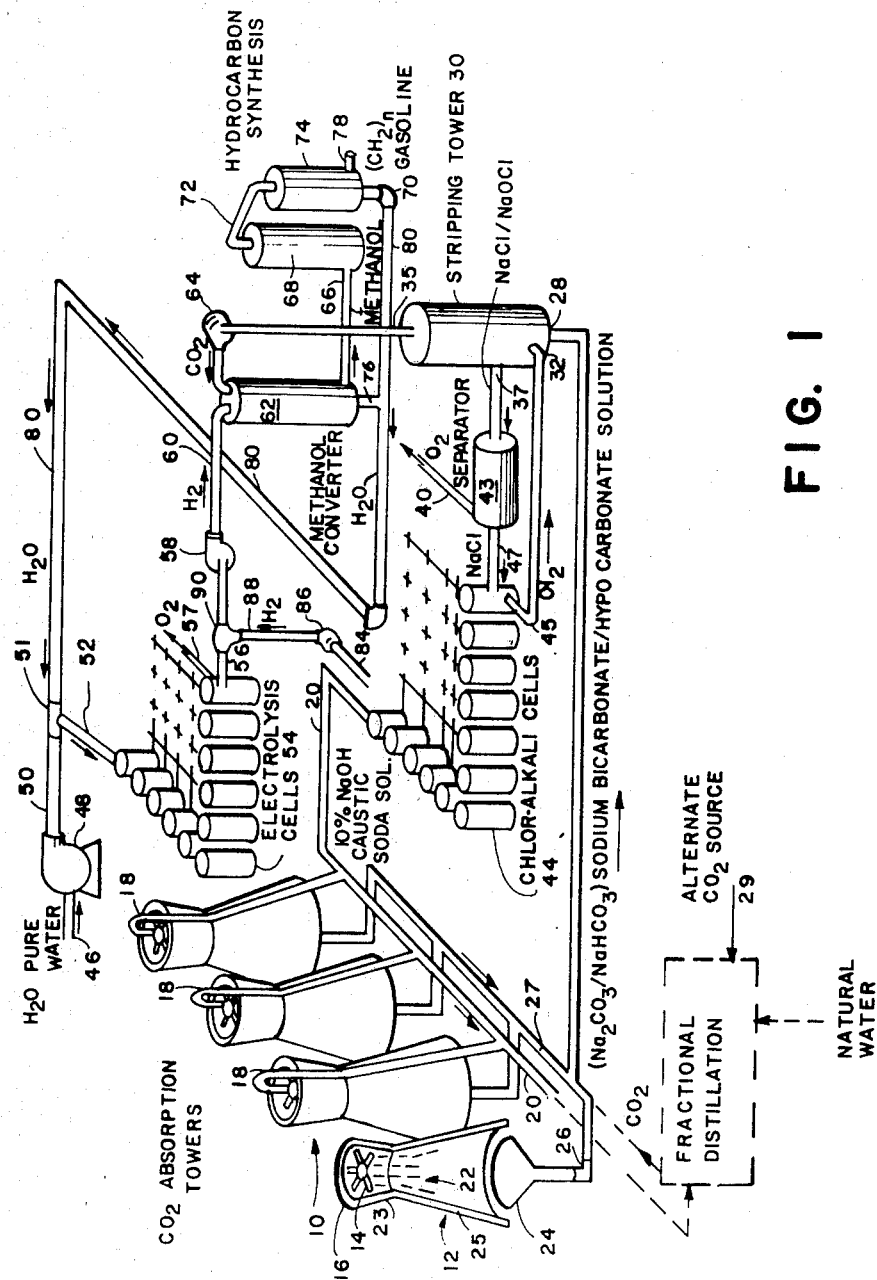
FIG. 1 is a mechanical schematic diagram of the present inventive process.

In a preferred embodiment, this invention consists of the fixation of the $CO_2$ present in the atmosphere (0.33 percent by volume) by the interaction of a weak base with the carbonic acid formed by the presence of $CO_2$ in moisture. This is a rather fast reaction resulting in the mixed salts of sodium bicarbonate ($Na_2CO_3$) and hypo carbonate ($NaHCO_3$) in a water solution. Alternately, the $CO_2$ may also be derived from natural water such as rivers, oceans, and lakes. This may be accomplished by conventional fractional distillation of the water to separate the $CO_2$ from other gases absorbed in the water. $CO_2$ constitutes $0.1 \times 10^{-3}$ Gm/cc by weight of natural water.

Referring to FIG. 1, the preferred method for obtaining the mixed salts of sodium bicarbonate and hypo carbonate is schematically shown. A number of $CO_2$ absorption towers, generally indicated by reference numeral 10, are characterized as frusto-conical constructions. FIGS. 1 and 3a show tower 12 in a cut-away view illustrating a fan 14 positioned at the upper inlet 16 of the tower. Pipes 18 are respectively connected to each of the tower fans and supply a 10 percent caustic soda solution (NaOH) to a respective fan 14 which has holes (not shown) in its blade structure for changing the state of the caustic soda solution to droplets 22, within the interior of each tower. In this respect, the droplet forming apparatus constitutes prior art since holes have been drilled in propeller blades for the release of deicing fluid. The caustic soda solution is fed to the towers 10 by a common supply pipe 20. During operation of the illustrated system in FIG. 1, air is induced to enter the top of each tower by the fan which is preferably electrically driven and which provides an axial flow through the tower. The droplets 22 of the NaOH solution are accelerated through a venturi 23 to promote mixing, and is then decelerated in a diffuser section 25 to relatively low velocities in order to avoid misting. The resulting $Na_2CO_3/NaHCO_3$ solution droplets are collected on a splashplate 24 at the base of the tower and is pumped through outlet pipe 26 to a common collection pipe 27 for all the towers. The base solution is then fed to inlet 28 of a $CO_2$ stripping tower 30 which may be a conventional bubble tower. The $Na_2CO_3/NaHCO_3$ solution may also be derived by supplying $CO_2$ from natural water instead of using the absorption towers. As previously mentioned, the $CO_2$ component may be derived by fractional distillation apparatus 29. The chemical equation expressing the reaction beteen the NaOH caustic soda solution and the $CO_2$ derived from air or water is expressed in the table of FIG. 2 line (b).

By way of example, the absorption tower 12 shown in FIG. 3a may typically be 180 feet in height and 40 feet in diameter at the upper inlet 16. The diffuser 25 may be configured at 6° while the airflow will equal 10–50 feet per second with a resulting "through-put" of $6\frac{3}{4}$ million standard cubic feet per minute per tower. The pressure differential between the upper inlet 16 and the lower outlet at the splashplate 24 will be approximately 1 atmosphere. An improvement upon the simple one atmosphere tower described above can be made by increasing the pressure within the tower to several atmospheres, since reaction rates of this type improve linearly with pressure. Viewing FIG. 3b, the electric motor fan may be replaced with a single stage compressor, and the tower's dimension foreshortened in direct proportion to the pressure ratio of that compressor. In order to power the compressor, an expander (turbine) is added to the base of the tower, which might also serve as a centrifugal droplet separator. Since neither the compressor nor the expander is 100 percent efficient, make-up power will have to be provided to the shaft connecting the two. Frustoconical tower 32 is seen to include a conventional compressor blade assembly 34 which, like the fan 14, has holes or openings (not shown) drilled therein which distribute the NaOH solution as droplets within the interior of the tower. The mentioned expander is shown by turbine blade assembly 36 located at the outlet of the tower 32. With the proper choice of dimensional specifications, the pressure drop in the tower 32 may be as great as four atmospheres and the flow rate through the tower will be comparable to that of the embodiment shown in FIG. 3a, namely, 10-50 feet per second. In order to step down the pressure in the tower 32, a frustoconical diffuser 38 is shown communicating with the lower outlet end of tower 32. A lower end of the diffuser 38 vents to the atmosphere. As droplets fall toward the lower outlet of tower 32, they impinge upon the turbine blade assembly 36 and a centrifugal effect forces droplets collecting on the turbine blade assembly to the lower sidewalls of the tower 32 and thereafter through the openings 40 to splashplate 42. The outlet pipe 26 collects the $Na_2CO_3$ solution as previously described in connection with FIGS. 1 and 3a.

A still further improvement conceived for the present invention which may reduce the size and improve the collection efficiency of a tower would be obtained through the use of ion attraction similar to those employed in smoke stack scrubbers common in combustion power plants and diagrammatically shown in FIG. 3b. Such a technique would customarily involve the imparting of an electrical charge, at a grid 39 to the NaOH solution droplets at the inlet to the tower, the opposite charge being imparted to the collection grid 41 at the outlet end of the tower. Such a technique might allow the droplets to move through the tower at higher speeds and still permit 100 percent recovery of the $Na_2CO_3/NaHCO_3$ solution.

In order to enhance the mixing of the NaOH droplets with air in a $CO_2$ absorption tower, cyclonic techniques may be employed. Such cyclonic techniques have the additional advantage of coalescing the droplets of $Na_2CO_3/NaHCO_3$ solution by centrifugal action imparted by a cyclonic fan structure. The apparatus for carrying out such a cyclonic technique may be of the type disclosed in U.S. Pat. No. 4,070,131 to Yen, assigned to the assignee of the present application. In order to reduce the height of the tower and still maintain good pressure recovery, the diffuser outlet angle of the $CO_2$ absorption tower can be increased from a normal 6 degrees to 15 degrees or more by incorporating, within the interior of a tower, a wind turbine as disclosed in U.S. Pat. No. 4,075,500 to Oman et al. and assigned to the assignee of the present application.

Referring once again to FIG. 1, the purpose of the stripping tower 30 is to catalytically remove $CO_2$ from the solution through the action of chlorine ($Cl_2$) on the solution. The requisite chlorine is supplied to tower 30 at tower inlet 32. $CO_2$ is drawn from the tower 30 through outlet pipe 35. The resulting solution is brine which flows from the tower 30 through pipe 37 to an oxygen separator 43 (boiler) which heats the NaCl (salt) and NaOCl in solution to cause the oxygen to vent to the atmosphere at outlet pipe 40. A pure NaCl solution (brine) results. One of the sources for heat, required by the $O_2$ separator 43 may be derived from the methanol and/or gasoline synthesis reactors explained in detail hereafter. The chemical equation relating to the $CO_2$ stripping tower 30 is shown on line (c) of FIG. 2, while the reaction of the oxygen separator is shown on line (d) of FIG. 2.

The brine solution is then pumped through the outlet pipe 47 to a battery of standard chlor-alkali cells 44 (Hooker cells) where electrical current is applied to produce $H_2$ at each cathode and $Cl_2$ at each anode. Such cells are available from Allied Chemical Company. The chemical equation representing the reaction in the cells 44 is represented by line (e) of the table shown in FIG. 2. As will be seen from the equation, a byproduct solution in the form of caustic soda (NaOH) results. This solution is piped back to the absorption towers 10 through pipe 20. Another byproduct from the cells 44 is $Cl_2$ which is fed back to the $CO_2$ stripping tower 30 through feedback pipe 45.

In order to complete the process, $H_2$ must be generated. This is accomplished when pure water is provided at inlet pipe 46 to pump 48 and thereafter to supply pipe 50 where a coupling 51 diverts the water flow to the electrolysis cells 54 via connecting pipe 52. The water provided in pipe 46 may be derived from natural water sources such as rivers, lakes, etc. In the event that ocean water is to be used, it must first be desalinized in accordance with known techniques which do not, per se, form a part of the present invention.

The electrolysis of distilled or fresh water to produce $H_2$ and $O_2$ is well-known art, practiced most frequently in nuclear submarines where breathing oxygen is obtained from such electrolysis. Appropriate electrolysis cells are comprised of a solid polymer electrolyte as developed by General Electric Company and disclosed in the General Electric Publication by L. J. Nuttall entitled "Production and Application of Electrolytic $H_2$ Present and Future," Apr. 6, 1979. At the outlet pipe 56 of the battery of cells is a vent outlet 57 from which the $O_2$ electrolysis component is vented to the atmosphere. A compressor 58 compresses the $H_2$ electrolysis component from the electrolysis cells 54 and delivers it to a first inlet of the previously mentioned prior art methanol converter 62. A compressor 64 compresses the $CO_2$ delivered from the $CO_2$ stripping tower 30 and both these gases, which have been compressed to a typical pressure of 100 atmospheres (1500 psi), are admitted to the methanol converter 62 which contains a copper catalyst which accelerates the combination of the two streams of gases to produce methanol (methyl alcohol—$CH_3OH$).

The $H_2$ derived from the chlor-alkali cells 44 is delivered to compressor 86 via supply pipe 84 and thereafter through connector pipe 88 to the T-connector 90. At this point, $H_2$ resulting from the chlor-alkali cells is added to the $H_2$ resulting from the electrolysis of $H_2O$ from the electrolysis cells 54 for ultimate delivery to the methanol converter 62. The chemical reaction resulting from the catalytic process in converter 62 is represented by step (f) of the table shown in FIG. 2.

The methanol derived from converter 62 flows through pipe 66 for collection as an end product or for subsequent hydrocarbon synthesis by the prior art technique previously mentioned. In brief, the synthesis begins in catalytic reactor vessel 68 which contains the catalyst zeolite. A resulting hydrocarbon liquid is then transferred through pipe 72 to a second separator vessel 74 which extracts water at outlet 70 and produces a synthetic hydrocarbon $(CH_2)_n$ at 78. The average molecular weight of these is dependent upon the pore size of the catalyst and/or the temperature/pressure level. Therefore, liquid products ranging from the "light" gasolines to "intermediate" kerosenes, and possibly even "heavier" heating oil can be synthesized. Thus, it is intended that the present invention satisfy the equation shown in line (g) of FIG. 2 where n ranges between approximately 4 and 10. The water extracted during the hydrocarbon synthesis is transferred from the outlet 70 of vessel 74 to supply pipe 80. This water is added to the water extracted at the outlet 76 of methanol converter 62 and is further added, at the coupling 51, to the water, fed to the electrolysis cells 54, externally through supply pump 48. Thus, the system recycles a portion of its water requirement. This is quite important for a tidal power plant or shipboard application where fresh water may be, or usually is, difficult to obtain.

A simplification to the described system may be accomplished by combining the stripping tower 30, oxygen separator 43 and chlor-alkali cells 44 into a multi-chambered reactor which eliminates external chlorine piping.

The hydrocarbon synthesis is an exothermic reaction and in regions of the world where air temperatures are low, and freezing of the weak caustic soda solution at the inlet of towers 10 would become a problem, the application of the exothermic waste heat to the incoming air would overcome the problem. It should be noted that the methanol conversion also generates waste heat which would be available for this purpose. The $O_2$ separator 43 requires heat which could be derived from either or both the hydrocarbon synthesis or the methanol conversion. The transfer of heat from these sources to either the towers or the $O_2$ separator would involve conventional heat transfer technology such as the use of radiators or heat pipes.

It will further be noted that once the cycle of the system illustrated in FIG. 2 begins, there is little need to add caustic soda and/or chlorine. If there is any need for make-up of these chemicals, a nearby source of salt water can be desalinized to produce NaOH and chlorine.

In order to accomplish the process constituting the invention, significant amounts of low-cost electrical power must be consumed, because it is conservatively estimated that the cycle efficiency (energy as compared with potential energy out) is between 25 and 37 percent. Electrical energy must be supplied to the fans 14 of the towers 10 as well as to the electrolysis cells 54 and the chlor-alkali cells 44. Additional power is consumed by the pumps and compressors illustrated in FIG. 1. It is envisioned that the most economical source of such significant power supplies is hydropower, although it is emphasized that this is not a limitation of the invention. Accordingly, alternate sources, such as solar energy, wind energy, tidal power, geothermal or nuclear power may be used. Electrical power from nuclear reactor equipped vessels could be employed for a shipboard system for synthesis of hydrocarbons. If power from a non-dedicated power plant is used, it may be used during off-peak hours to reduce costs.

It should be understood that the invention is not limited to the exact details of construction shown and described herein for obvious modifications will occur to persons skilled in the art.

We claim:

1. A process for manufacturing synthetic hydrocarbons fuels from the synthesis of $CO_2$ and $H_2$, the process comprising the steps:
    subjecting a NaOH solution to $CO_2$ present in air, resulting in production of $Na_2CO_3$ and $NaHCO_3$;
    reacting the resulting solution with $Cl_2$
    (a) causing stripping of the $CO_2$ and
    (b) forming brine and NaOCl;
    separating the oxygen from the NaOCl whereby additional brine results;
    electrolyzing the brine to form $H_2$, $Cl_2$ and NaOH;
    recycling the resulting $Cl_2$ for further stripping of $CO_2$;
    recycling the resulting NaOH for further reaction with $CO_2$;
    reacting the stripped $CO_2$ and the $H_2$ from the electrolyzed brine to form methanol and water; and
    separating the methanol and water thus permitting collection of the methanol.

2. The method set forth in claim 1 together with the step of synthesizing hydrocarbon fuel from the separated methanol.

3. The method set forth in claim 1 together with the step of recycling the water, separated from the methanol, for electrolysis which produces $H_2$ which is itself recycled for reaction with stripped $CO_2$ to form the methanol.

4. The method set forth in claim 2 together with the step of recycling the water, separated from the methanol, for electrolysis which produces $H_2$ which is itself recycled for reaction with stripped $CO_2$ to form the methanol.

5. The method set forth in claim 4 wherein the step of subjecting a NaOH solution to $CO_2$ occurs during the passage of solution droplets through air.

6. The method set forth in claim 4 together with the step of transferring exothermic heat, derived from the methanol and hydrocarbon producing steps, to the NaOCl for accelerating the separation of $O_2$ therefrom.

7. The method set forth in claim 5 together with the step of transferring exothermic heat, derived from the methanol and hydrocarbon producing steps, for preheating the NaOH solution thereby preventing it from freezing.

* * * * *